United States Patent
Kruck et al.

(10) Patent No.: US 11,883,522 B2
(45) Date of Patent: Jan. 30, 2024

(54) AGENT FOR DYEING KERATINOUS MATERIAL, CONTAINING AMINOSILICONE, A CHROMOPHORIC COMPOUND AND PHOSPHOROUS-CONTAINING SURFACTANT

(71) Applicant: Henkel AG & Co. KGaA, Duesseldorf (DE)

(72) Inventors: Constanze Kruck, Grevenbroich (DE); Sandra Hilbig, Bochum (DE); Melanie Moch, Dormagen (DE); Susanne Dickhof, Viersen (DE); Daniela Kessler-Becker, Leverkusen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/780,434

(22) PCT Filed: Sep. 14, 2020

(86) PCT No.: PCT/EP2020/075598
§ 371 (c)(1),
(2) Date: May 26, 2022

(87) PCT Pub. No.: WO2021/104703
PCT Pub. Date: Jun. 3, 2021

(65) Prior Publication Data
US 2023/0025953 A1 Jan. 26, 2023

(30) Foreign Application Priority Data
Nov. 26, 2019 (DE) .......................... 102019218231.3

(51) Int. Cl.
*A61Q 5/10* (2006.01)
*A61K 8/898* (2006.01)
*A61K 8/37* (2006.01)
*A61K 8/55* (2006.01)

(52) U.S. Cl.
CPC .............. *A61K 8/898* (2013.01); *A61K 8/375* (2013.01); *A61K 8/55* (2013.01); *A61Q 5/10* (2013.01); *A61K 2800/43* (2013.01)

(58) Field of Classification Search
CPC .......... A61K 8/898; A61K 8/375; A61K 8/55; A61K 2800/43; A61K 8/556; A61Q 5/10; A61Q 5/065
USPC ............................................................ 8/405
See application file for complete search history.

(56) References Cited

U.S. PATENT DOCUMENTS

| | | | | | |
|---|---|---|---|---|---|
| 2010/0083446 | A1* | 4/2010 | Brun | ...................... | A61K 8/891 8/405 |
| 2014/0298594 | A1* | 10/2014 | Weser | .................... | A61K 8/556 8/405 |

FOREIGN PATENT DOCUMENTS

| | | | | |
|---|---|---|---|---|
| DE | 19613941 | A1 | 10/1997 | |
| DE | 102011085416 | A1 | 6/2012 | |
| DE | 102014221533 | A1 | 4/2016 | |
| EP | 2168633 | A2 | 3/2010 | |
| FR | 2944967 | A1 | 11/2010 | |
| WO | WO 2011024300 | A1 * | 3/2011 | ............... A61Q 5/10 |
| WO | 2013068979 | A2 | 5/2013 | |
| WO | WO 2017108828 | A1 * | 6/2017 | ............. A61Q 5/065 |

\* cited by examiner

*Primary Examiner* — Eisa B Elhilo
(74) *Attorney, Agent, or Firm* — Lorenz & Kopf, LLP

(57) ABSTRACT

It is an object of the present disclosure to provide an agent for coloring keratinous material, in particular human hair, comprising
(a1) at least one amino-functionalized silicone polymer, and
(a2) at least one pigment, and
(a3) at least one phosphorus-comprising organic compound.
A second subject matter is a method for dyeing keratin material, wherein the agent is applied to the keratin material.

18 Claims, No Drawings

AGENT FOR DYEING KERATINOUS MATERIAL, CONTAINING AMINOSILICONE, A CHROMOPHORIC COMPOUND AND PHOSPHOROUS-CONTAINING SURFACTANT

CROSS-REFERENCE TO RELATED APPLICATION

This application is a U.S. National-Stage entry under 35 U.S.C. § 371 based on International Application No. PCT/EP2020/075598, filed Sep. 14, 2020, which was published under PCT Article 21(2) and which claims priority to German Application No. 102019218231.3, filed Nov. 26, 2019, which are all hereby incorporated in their entirety by reference.

TECHNICAL FIELD

The subject of the present application is an agent for coloring keratinous material, in particular human hair, which comprises at least one amino-functionalized silicone polymer (a1), at least one pigment (a2) and at least one phosphorus-comprising organic compound (a3).

A second object of this application is a method for dyeing keratinous material, in particular human hair, wherein an agent of the first object of the present disclosure is applied to the keratinous material, allowed to act and then washed out again with water.

BACKGROUND

Changing the shape and color of keratinous material, especially human hair, is a key area of modern cosmetics. To change the hair color, the expert knows various coloring systems depending on the coloring requirements. Oxidation dyes are usually used for permanent, intensive dyeings with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes have very long-lasting dyeing results.

When direct dyes are used, ready-made dyes diffuse from the colorant into the hair fiber. Compared to oxidative hair dyeing, the dyeings obtained with direct dyes have a shorter shelf life and quicker wash ability. Dyes with direct dyes usually remain on the hair for a period of between 5 and 20 washes.

The use of color pigments is known for short-term color changes on the hair and/or skin. Pigments or color pigments are understood to be insoluble, color-imparting substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

If the user wants particularly long-lasting dyeings, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes. One viable alternative coloring system that has recently come increasingly into focus is based on the use of colored pigments.

Coloring with pigments offers several significant advantages. Since the pigments only attach themselves to the keratin materials, especially the hair fibers, from the outside, the damage associated with the dyeing process is particularly low. Furthermore, colorations that are no longer desired can be removed quickly and easily without leaving any residue, thus offering the user the possibility of returning to his original hair color immediately and without significant effort. Especially for those consumers who do not want to recolor their hair regularly, this coloring process is therefore particularly attractive.

In previous work, the problem of low durability of this staining system was addressed. In this context, it was found that the wash fastness of the color results obtained with pigments could be improved by combining the pigments with certain amino-functionalized silicone polymers. In addition, by selecting particularly well-suited pigments and pigment concentrations on dark hair, it was possible to achieve a lighter color result, so that with this coloring system it was even possible to lighten hair, which until then had only been possible with oxidative hair treatment agents (bleaching or bleaching agents).

In addition to these many advantages, however, the pigment-based coloring system still has some disadvantages. Since both the pigments and the amino silicones that immobilize the pigments are deposited on the surface of the hair fiber, its surface structure is modified by the formation of a film. Depending on the thickness of the film formed, this modification may also be associated with a change in the haptic impression of the hair fibers, ranging from the feeling of having weighed-down or greasy hair to a rough, shaggy or straw-like feel to the hair.

BRIEF SUMMARY

Agents and processes for dyeing keratinous material are provided herein. In an embodiment, an agent for dyeing keratinous material comprises:
 (a1) at least one amino-functionalized silicone polymer,
 (a2) at least one pigment, and
 (a3) at least one phosphorus-containing organic compound.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description. It is to be appreciated that all numerical values as provided herein, save for the actual examples, are approximate values with endpoints or particular values intended to be read as "about" or "approximately" the value as recited.

It was the task of the present disclosure to provide a pigment-based coloring system that enables intensive color results with good hair feel. The search was on for a technology that would allow colored pigments to be fixed to the hair as permanently as possible, without the hair feeling weighed down, greasy, unnatural, straw-like or occupied. A particular focus of the task was to achieve intense, washable color results with a good hair feel at the same time.

Surprisingly, it has been found that this task can be solved if keratinous materials, in particular hair, are colored with an agent comprising at least one amino-functionalized silicone polymer (a1), at least one pigment (a2), and at least one phosphorus-comprising organic compound (a3).

A first object of the present disclosure is an agent for coloring keratinous material, in particular human hair, comprising
- (a1) at least one amino-functionalized silicone polymer, and
- (a2) at least one pigment, and
- (a3) at least one phosphorus-comprising organic compound.

In the course of the work carried out on the present disclosure, it has surprisingly been shown that very intense and washfast colorations can be obtained with the use of colorants comprising at least one amino silicone (a1) and at least one pigment (a2). If (a1) and (a2) were now combined with at least one phosphorus-comprising organic compound (a3), the hair feel of the dyed hair was improved at the same time.

These positive effects were observed when the phosphorus-comprising organic compound (a3) was a surfactant comprising at least one phosphorus atom. Here, the improvement in hair feel was achieved without sacrificing coloring performance.

Keratinic Material

Keratinous material includes hair, skin, nails (such as fingernails and/or toenails). Wool, furs and feathers also fall under the definition of keratinous material. Preferably, keratinous material is understood to be human hair, human skin and human nails, especially fingernails and toenails. Keratinous material is understood to be human hair.

Coloring Agent

The term "agent for coloring" is used in the context of this present disclosure for a coloring of the keratin material, of the hair, caused using pigments. In this coloring process, the pigments are deposited as coloring compounds in a particularly homogeneous, uniform and smooth film on the surface of the keratin material.

Amino-Functionalized Silicone Polymers (a1)

As a first essential ingredient (a1), the agent as contemplated herein comprises at least one amino-functionalized silicone polymer. The amino-functionalized silicone polymer may alternatively be referred to as amino silicone or amodimethicone.

Silicone polymers are macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than 10 g/mol, preferably not more than 106 g/mol, and particularly preferably not more than 105 g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, beneficial effects could be obtained with amino-functionalized silicone polymers (a1) if they carry at least one primary, at least one secondary and/or at least one tertiary amino group. However, dyeings with the best wash fastness were observed when an amino-functionalized silicone polymer (a1) was used in agent (a), which comprises at least one secondary amino group.

In a very particularly preferred embodiment, an agent as contemplated herein the agent comprises at least one amino-functionalized silicone polymer (a1) having at least one secondary amino group.

The secondary amino group(s) may be located at various positions on the amino-functionalized silicone polymer. Particularly beneficial effects were found when an amino-functionalized silicone polymer (a1) was used that has at least one, preferably several, structural units of the formula (Si amino).

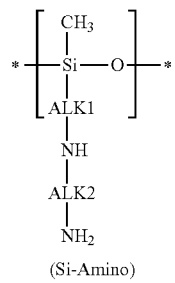

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, an agent as contemplated herein comprises at least one amino-functionalized silicone polymer (a1) comprising at least one structural unit of the formula (Si amino),

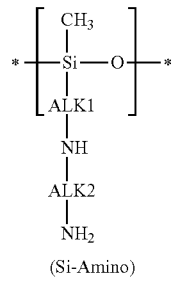

(Si-Amino)

where
ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (a1), so that the silicone polymer comprises multiple structural units of the formula (Si amino).

Particularly well-suited amino-functionalized silicone polymers (a1) with at least one secondary amino group are listed below.

Dyeings with the best wash fastnesses could be obtained if in the process as contemplated herein at least one agent (a) was applied to the keratinous material which comprises at least one amino-functionalized silicone polymer (a1) comprising structural units of the formula (Si-I) and of the formula (Si-II)

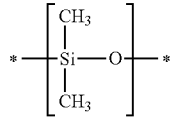

(Si-I)

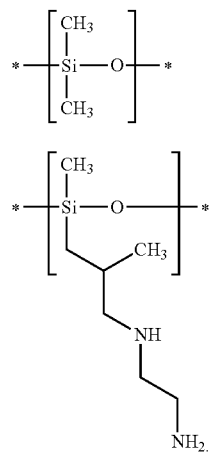

(Si-II)

In a further explicitly quite particularly preferred embodiment, an agent as contemplated herein comprises at least one amino-functionalized silicone polymer (a1) comprising structural units of the formula (Si-I) and of the formula (Si-II)

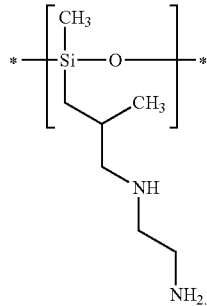

(Si-I)

(Si-II)

A corresponding amino functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8.

In another preferred embodiment, an agent as contemplated herein comprises at least one amino-functional silicone polymer (a1) of the formula of the formula (Si-III),

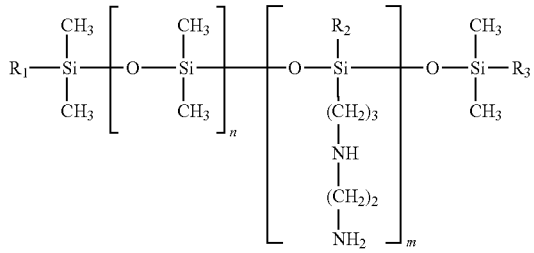

(Si-III)

where m and n mean numbers chosen so that the sum (n+m) is in the range 1 to 1000, n is a number in the range 0 to 999 and m is a number in the range 1 to 1000, R1, R2 and R3, which are the same or different, denote a hydroxy group or a $C_{1-4}$ alkoxy group, wherein at least one of R1 to R3 represents a hydroxy group;

A further agent preferred as contemplated herein comprises at least amino-functional silicone polymer (a1) of the formula of the formula (Si-IV),

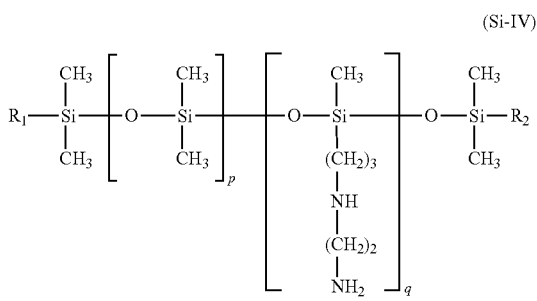
(Si-IV)

located in the
- p and q mean numbers chosen so that the sum (p+q) is in the range 1 to 1000,
- p is a number in the range 0 to 999 and q is a number in the range 1 to 1000,
- R1 and R2, which are different, denote a hydroxy group or a $C_{1-4}$ alkoxy group, at least one of R1 to R2 denoting a hydroxy group.

The silicones of the formulas (Si-III) and (Si-IV) differ in the grouping at the Si atom, which carries the nitrogen-comprising group: In formula (Si-III), R2 represents a hydroxy group or a $C_{1-4}$ alkoxy group, while the radical in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1—Si(CH$_3$)$_2$ group is necessarily bonded to an —[O—Si(CH$_3$)$_2$] grouping.

Agents as contemplated herein which contain at least one amino-functional silicone polymer (a1) of the formula of the formula (Si-V) have also proved to be particularly effective with respect to the desired effects

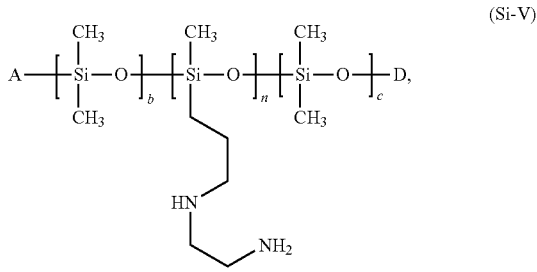
(Si-V)

located in the
- A represents a group —OH, —O—Si(CH$_3$)$_3$, —O—Si(CH$_3$)$_2$OH, —O—Si(CH$_3$)$_2$OCH$_3$,
- D represents a group —H, —Si(CH$_3$)$_3$, —Si(CH$_3$)$_2$OH, —Si(CH$_3$)$_2$OCH$_3$,
- b, n and c stand for integers between 0 and 1000, with the specifications
n>0 and b+c>0
at least one of the conditions A=—OH or D=—H is fulfilled.

In the above formula (Si-V), the individual siloxane units are statistically distributed with the indices b, c and n, i.e., they do not necessarily have to be block copolymers.

Agent (a) may further comprise one or more different amino-functionalized silicone polymers represented by the formula (Si-VI)

$$M(R_aQ_bSiO_{(4-a-b)/2})_x(R_cSiO_{(4-c)/2})_yM$$ (Si-VI)

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical comprising at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-comprising radicals, such as mercaptoethyl, mercaptopropyl, mercaptohexyl, mercaptophenyl and the like; preferably R is an alkyl radical comprising from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional radical comprising at least one amino functional group. One formula for Z is NH(CH$_2$)$_z$NH$_2$, where z is 1 or more. Another formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$ radical. Another formula for Z is —N(CH$_2$)$_z$(CH$_2$)$_{zz}$NX$_2$ or —NX$_2$, wherein each X of X2 is independently selected from the group of hydrogen and alkyl groups having 1 to 12 carbon atoms, and zz is 0. Q is most preferably a polar, amine-functional radical of the formula —CH$_2$CH$_2$CH$_2$NHCH$_2$CH$_2$NH 2. In the formulas, "a" takes values ranging from about 0 to about 2, "b" takes values ranging from about 2 to about 3, "a"+"b" is less than or equal to 3, and "c" is a number ranging from about 1 to about 3. The molar ratio of $R_aQ_b$ SiO$_{(4-a-b)/2}$ units to $R_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, an agent as contemplated herein comprises at least one amino-functional silicone polymer of the formula (Si-VII)

$$R'_aG_{3-a}\text{-Si}(OSiG_2)_n\text{-}(OSiG_bR'_{2-b})_m\text{—O—}SiG_{3-a}\text{-}R'_a$$ (Si-VII), wherein:
G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;
a stands for a number between 0 and 3, especially 0;
b stands for a number between 0 and 1, especially 1,
m and n are numbers whose sum (m+n) is between 1 and 2000, preferably between 50 and 150, where n preferably assumes values from 0 to 1999 and from 49 to 149 and m preferably assumes values from 1 to 2000, from 1 to 10,
R' is a monovalent radical selected from
-Q-N(R")—CH$_2$—CH$_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—CH$_2$—CH$_2$—N$^+$R"H$_2$A$^-$,
where each Q is a chemical bond, —CH$_2$—, —CH$_2$CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—,
R" represents identical or different radicals selected from the group of —H, -phenyl, -benzyl, —CH$_2$—CH(CH$_3$)Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion preferably selected from chloride, bromide, iodide or methosulfate.

In another preferred embodiment, an agent as contemplated herein comprises at least one amino-functional silicone polymer (a1) of the formula (Si-VIIa),

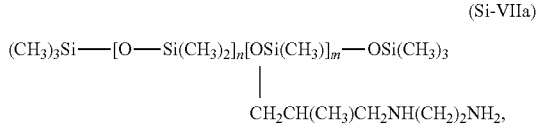

(Si-VIIa)

wherein m and n are numbers whose sum (m+n) is between 1 and 2000, preferably between 50 and 150, n preferably assuming values from 0 to 1999 and from 49 to 149, and m preferably assuming values from 1 to 2000, from 1 to 10.

According to the INCI declaration, these silicones are called trimethylsilylamodimethicones.

In the context of a further preferred embodiment, an agent as contemplated herein comprises at least one amino-functional silicone polymer (a1) of the formula (Si-VIIb)

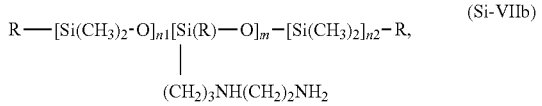

(Si-VIIb)

in which R represents —OH, —O—CH$_3$ or a —CH$_3$ group and m, n1 and n2 are numbers whose sum (m+n1+n2) is between 1 and 2000, preferably between 50 and 150, the sum (n1+n2) preferably assuming values from 0 to 1999 and from 49 to 149 and m preferably assuming values from 1 to 2000, from 1 to 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above 0.25 meq/g, preferably above 0.3 meq/g and above 0.4 meq/g. The amine number represents the milliequivalents of amine per gram of the amino-functional silicone. It can be determined by titration and expressed in the unit mg KOH/g.

Furthermore, agent (a) comprising a special 4-morpholinomethyl-substituted silicone polymer (a1) are also suitable. This amino-functionalized silicone polymer comprises structural units of the formulae (SI-VIII) and of the formula (Si-IX)

(Si-VIII)

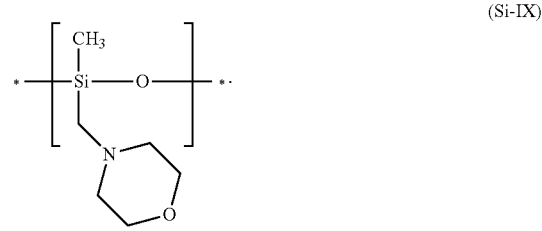

(Si-IX)

Corresponding 4-Morpholinomethyl-Substituted Silicone Polymers are Described Below.

A corresponding amino-functionalized silicone polymer is available under the name of
Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

(Si-VIII)

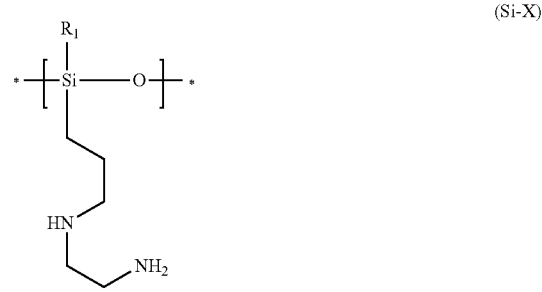

(Si-X)

(Si-IX)

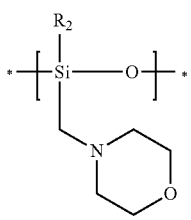

in which
R1 is —CH₃, —OH, —OCH₃, —O—CH₂CH₃, —O—CH₂CH₂CH₃, or —O—CH(CH₃)₂;
R2 is —CH₃, —OH, or —OCH₃.

Particularly preferred agent (a) as contemplated herein contain at least one 4-morpholinomethyl-substituted silicone of the formula (Si-XI)

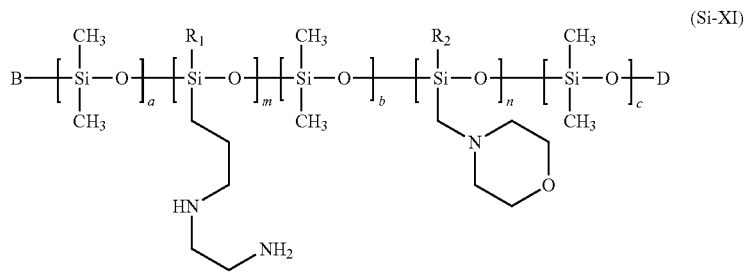

located in the
R1 is —CH₃, —OH, —OCH₃, —O—CH₂CH₃, —O—CH₂CH₂CH₃, or —O—CH(CH₃)₂;
R2 is —CH₃, —OH, or —OCH₃.
B represents a group —OH, —O—Si(CH₃)₃, —O—Si(CH₃)₂OH, —O—Si(CH₃)₂OCH₃,
D represents a group —H, —Si(CH₃)₃, —Si(CH₃)₂OH, —Si(CH₃)₂OCH₃, a, b and c stand independently for integers between 0 and 1000, with the condition a+b+c>0
m and n independently of each other stand for integers between 1 and 1000
with the proviso that
at least one of the conditions B=—OH or D=—H is fulfilled,
the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed.

The silicones used as contemplated herein represented by formula (Si-VI) can be trimethylsilyl-terminated (D or B=—Si(CH₃)₃), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—Si(CH₃)₂OH and D=—Si(CH₃)₃
B=—O—Si(CH₃)₂OH and D=—Si(CH₃)₂OH
B=—O—Si(CH₃)₂OH and D=—Si(CH₃)₂OCH₃
B=—O—Si(CH₃)₃ and D=—Si(CH₃)₂OH
B=—O—Si(CH₃)₂OCH₃ and D=—Si(CH₃)₂OH to everyone. These silicones lead to exorbitant improvements in the hair properties of the hair treated with the agents of the present disclosure, and to a seriously improved protection in oxidative treatment.

It has been found to be particularly advantageous if the agent as contemplated herein comprises the amino-functionalized silicone polymer(s) (a1) in certain quantity ranges. Particularly satisfactory results were obtained when the agent included—based on the total weight of the agent—a total amount of 0.1 to 8.0 wt. %, preferably 0.2 to 5.0 wt. %, more preferably 0.3 to 3.0 wt. %, and most preferably 0.4 to 2.5 wt. %.

In another particularly preferred embodiment, an agent as contemplated herein comprises—based on the total weight of the agent—one or more amino-functionalized silicone polymers (a1) in a total amount of from 0.1 to 8.0 wt. %, preferably from 0.2 to 5.0 wt. %, more preferably from 0.3 to 3.0 wt. % and very particularly preferably from 0.4 to 2.5 wt. %.

Pigments (a2)

As a second essential component, the agent as contemplated herein comprises at least one colorant compound selected from the group of pigments (a2).

For the purposes of the present disclosure, colorant compounds are substances capable of imparting a coloration to the keratin material. As contemplated herein, the coloring compounds are selected from the group of pigments.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein comprises at least one colorant compound (a2) from the group comprising inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein comprises at least inorganic pigment (a2), which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, an agent as contemplated herein comprises at least one pigment (a2) selected from mica- or mica-based pigments which are reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:
- Unipure Red LC 381 EM, Sensient CI 77491 (Iron Oxides), Silica
- Unipure Black LC 989 EM, Sensient, CI 77499 (Iron Oxides), Silica
- Unipure Yellow LC 182 EM, Sensient, CI 77492 (Iron Oxides), Silica In a further embodiment, the agent as contemplated herein may also contain one or more colorant compounds (a2) from the group comprising organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyrrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, an agent as contemplated herein comprises at least one organic pigment (a2) which is preferably selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the agent is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, 14 to 30 µm. The mean particle size $D_{50}$, for example, can be determined using dynamic light scattering (DLS).

The pigment(s) (a2) constitute the second essential of the agent as contemplated herein and are preferably used in the agent in certain ranges of amounts. Particularly satisfactory results were obtained when the agent included—based on the total weight of the agent—one or more pigments (a2) in a total amount of 0.01 to 10.0 wt. %, preferably 0.1 to 5.0 wt. %, further preferably 0.2 to 2.5 wt. % and very preferably 0.25 to 1.5 wt. %.

In another very particularly preferred embodiment, an agent as contemplated herein comprises—based on the total weight of the agent—one or more pigments (a2) in a total amount of from 0.01 to 10.0 wt. %, preferably from 0.1 to 5.0 wt. %, more preferably from 0.2 to 2.5 wt. % and very particularly preferably from 0.25 to 1.5 wt. %.

As a further optional component, the agents as contemplated herein could also additionally contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, an agent as contemplated herein additionally comprises at least one colorant compound selected from the group of anionic, nonionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO—, —SO$_3$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

A feature of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In a further embodiment, an agent for dyeing keratinous material comprises at least one anionic direct dye selected from the group of the nitrophenylenediamines, the nitroaminophenols, the azo dyes, the anthraquinone dyes, the triarylmethane dyes, the xanthene dyes the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C.015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodium-salt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Real red D, FD&C Red Nr. 2, Food Red 9, Naphthol red S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C.53, CI 45410), Acid Red 95 (CI 45425, Erythrosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C.063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3 (2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trisodium salt of 7-hydroxy-8-[(E)-(4-sulfonato-1-naphthyl)-diazenyl)]-1,3-naphthalene disulfonate and has a remarkably high water solubility of more than 20 wt. %.

Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl) benzoic acid, whose solubility in water is indicated as greater than 10 g/L (25° C.).

Acid Blue 9 is the disodium salt of 2-({4-[N-ethyl(3-sulfonatobenzyl]amino]phenyl} {4-[(N-ethyl(3-sulfonatobenzyl)imino]-2,5-cyclohexadien-1-ylidene}methyl)-benzenesulfonate and has a solubility in water of more than 20 wt. % (25° C.).

In a further embodiment, an agent as contemplated herein comprises at least one direct dye selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct-acting dye or dyes can be used in various amounts in the agents, depending on the desired color intensity. Satisfactory results were obtained when the agent comprises—based on the total weight of the agent—one or more direct dyes in a total amount of 0.01 to 10.0 wt. %, preferably 0.1 to 8.0 wt. %, more preferably 0.2 to 6.0 wt. % and most preferably 0.5 to 4.5 wt. %.

Furthermore, the agent may also contain, as an additional optional component, a coloring compound selected from the group of photochromic or thermochromic dyes.

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

The agent may contain—based on the total weight of the agent—one or more photochromic and/or thermochromic dyes in a total amount of from 0.01 to 10.0 wt. %, preferably from 0.1 to 8.0 wt. %, more preferably from 0.2 to 6.0 wt. % and most preferably from 0.5 to 4.5 wt. %.

Organic Compounds Comprising Phosphorus (a3)

As a third essential ingredient (a3), the agents as contemplated herein contain at least one phosphorus-comprising organic compound.

Phosphorus-comprising organic compounds are organic compounds that have at least one phosphorus atom. In other words, phosphorus-comprising organic compounds are understood to be the substances comprising at least one carbon atom and at least one phosphorus atom.

The following have proven to be particularly well suited for solving the task as contemplated herein phosphorus-comprising organic compounds (a3) were found to possess emulsifying properties and thus represent a phosphorus-comprising surfactant.

In the context of a further very particularly preferred embodiment, an agent as contemplated herein comprises at least one phosphorus-comprising emulsifier (a3).

In other words, in the context of a further very particularly preferred embodiment, an agent as contemplated herein comprises at least one phosphorus-comprising surfactant (a3).

The term surfactants refer to surface-active substances. A distinction is made between anionic surfactants comprising a hydrophobic radical and a negatively charged hydrophilic head group, amphoteric surfactants, which carry both a negative and a compensating positive charge, cationic surfactants, which in addition to a hydrophobic radical have a positively charged hydrophilic group, and non-ionic surfactants, which have no charges but strong dipole moments and are strongly hydrated in aqueous solution.

As a hydrophobic radical, the surfactants may comprise, for example, a long-chain alkyl group, for example a $C_{12}$-$C_{30}$ alkyl group or a $C_{12}$-$C_{24}$ alkyl group. This alkyl group can be linear or branched, saturated or mono- or polyunsaturated.

In the context of the present disclosure, a phosphorus-comprising surfactant is understood to mean a surfactant which has at least one phosphorus atom. This phosphorus atom can, for example, be part of a phosphate group or phosphonate group.

If a phosphate group is present, it may be attached to the hydrophobic radical of the surfactant via a covalent bond between an oxygen atom of the phosphate group and a C atom. In this case, the phosphorus-comprising surfactant is an organic phosphoric acid ester. In the monoesters of phosphoric acid, one oxygen atom of the phosphate group is esterified with a hydrophobic radical. However, the phosphorus-comprising surfactants can also be in the form of di-esters, where two oxygen atoms of the phosphate group are esterified with two hydrophobic radicals. These mono- and di-phosphoric acid esters can be used either in free form or in the form of their salts, for example in the form of their sodium, potassium or ammonium salt.

The phosphoric acid esters may also be alkoxylated, in which case one or more alkoxy groups, especially ethoxy groups, are located between the phosphoric acid group and the hydrophobic radical(s).

If a phosphonate group is present in the surfactant, it may be attached to the hydrophobic radical of the surfactant via a covalent bond between the phosphorus atom and a C atom. In this case, the phosphorus-comprising surfactant is an organic phosphonic acid, which can be used either in the form of its acid or also in the form of its salt, for example in the form of its sodium, potassium or ammonium salt.

Depending on their degree of substitution, the phosphoric esters or phosphonic acids described above are anionic phosphorus-comprising surfactants. Particularly beneficial effects could be achieved with anionic phosphorus-comprising surfactants, for which reason they are especially preferred.

In the context of a further very particularly preferred embodiment, an agent as contemplated herein comprises at least one anionic phosphorus-comprising surfactant (a3).

As explicitly particularly good in terms of improvement of the hair feeling have proved Alkyl phosphoric esters (a3) of formula (I) have been shown,

where
- $R_1$, $R_2$ and $R_3$ are independently hydrogen, an alkali metal cation, an ammonium ion or a radical of formula (II)

- m and n independently stand for an integer between 0 and 20, and
- R4 is a saturated or unsaturated, branched or unbranched $C_{12-24}$ alkyl radical, with the proviso that at least one of the radicals $R_1$, $R_2$ or $R_3$ is a radical of the formula (II).

In the context of a further very particularly preferred embodiment, an agent as contemplated herein comprises at least one alkyl phosphoric acid ester (a3) of the formula (I)

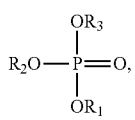  (I)

where
$R_1$, $R_2$ and $R_3$ are independently hydrogen, an alkali metal cation, an ammonium ion or a radical of formula (II)

  (II), m and n independently of each other stand for an integer from 0 to 20, and
R4 is a saturated or unsaturated, branched or unbranched $C_{12-24}$ alkyl radical,
with the proviso that at least one of the radicals $R_1$, $R_2$ or $R_3$ is a radical of the formula (II).

In the alkyl phosphoric esters (a3) of formula (I), R1, R2 and R3 are independently hydrogen, an alkali metal cation, an ammonium ion or a radical of formula (II)

  (II)

Here, there is the proviso that at least one of the radicals $R_1$, $R_2$ or $R_3$ is a radical of the formula (II).

In one embodiment, it has been found to be particularly preferred if R1 is a radical of formula (II) and the other two radicals R2 and R3 are a hydrogen atom, an alkali metal cation such as $Na^+$ or $K^+$, or an ammonium ion $(NH_4)^+$.

In a further embodiment, it has further been found to be particularly preferred if R1 and R2 independently represent a radical of formula (II) and the radical R3 represents a hydrogen atom, an alkali metal cation such as a sodium cation $(Na^+)$ or a potassium cation $(K^+)$ or an ammonium ion $(NH_4)^+$.

In the radical of formula (II), the indices m and n independently represent an integer from 0 to 20.

m indicates the number of ethoxy groups located between the phosphoric acid unit and the hydrophobic radical R4. Preferably, m stands for an integer from 0 to 10. Particularly preferably, m stands for the number 0, i.e., in this case the corresponding phosphorus-comprising surfactant is not ethoxylated.

n indicates the number of proxy groups located between the phosphoric acid moiety and the hydrophobic radical R4. Preferably, n stands for an integer from 0 to 20. Particularly preferably, n stands for the number 0, i.e., in this case the corresponding phosphorus-comprising surfactant is not propoxylated.

In each grouping of formula (II), the radical R4 represents a hydrophobic radical which is in the form of a long chain alkyl chain. R4 represents a saturated or unsaturated, branched or unbranched $C_{12-24}$ alkyl radical.

Particularly preferably, R4 represents a saturated, unbranched $C_{12-24}$ alkyl radical.

Very preferably, R4 represents a saturated, unbranched $C_{12-20}$ alkyl radical.

If two or more radicals from R1, R2 and R3 represent a grouping of formula (II), the respective radicals R4 may be the same or different.

In the context of a further very particularly preferred embodiment, an agent as contemplated herein comprises at least one alkyl phosphoric acid ester (a3) of the formula (I), where
$R_1$ is a radical of the formula (II), and
$R_2$ and $R_3$ independently represent a hydrogen atom, an alkali metal cation or an ammonium ion,
m and n stand for the number 0, and
$R_4$ is a saturated or unsaturated, branched or unbranched $C_{12-24}$ alkyl radical, In the context of a further very particularly preferred embodiment, an agent as contemplated herein comprises at least one alkyl phosphoric ester (a3) of the formula (I), where
$R_1$ and $R_2$ independently of one another are a radical of the formula (II), and
$R_3$ represents a hydrogen atom, an alkali metal cation or an ammonium ion,
m and n independently of each other stand for an integer from 0 to 10, and
$R_4$ is a saturated or unsaturated, branched or unbranched $C_{12-24}$ alkyl radical, If one or more radicals R1, R2 and/or R3 represent an alkali metal cation or an ammonium ion, then the phosphate group is present in the form of its salt, i.e., the negatively charged oxygen atom is neutralized by the presence of a corresponding equivalent of a positively charged cation (sodium cation, potassium cation or ammonium cation).

$C_{12-24}$ alkyl phosphoric acid esters or salts of $C_{12-24}$ alkyl phosphoric acid esters preferred as contemplated herein are selected from the monoesters of phosphoric acid with lauryl alcohol, tridecyl alcohol, isotridecyl alcohol, myristyl alcohol, pentadecyl alcohol, cetyl alcohol, palmityl alcohol, isocetyl alcohol, isostearyl alcohol, stearyl alcohol, oleyl alcohol, elaidyl alcohol, linoleyl alcohol, Linolenyl alcohol, nonadecyl alcohol, arachyl alcohol, gadoleyl alcohol or arachidonic alcohol, which is used as the alkali metal, alkaline earth metal, ammonium, alkylammonium, alkanolamine or glucammonium salt, preferably as the sodium, potassium, alkanolamine, trialkylammonium, triethanolamine, 2-amino 1-butanol, 2-amino-2-methyl-1-propanol, 2-amino-2-methyl-1,3-propanediol, 2-amino-2-ethyl-1,3-propanediol or tris(hydroxymethyl) aminomethane salt and as a salt of the basic amino acids ornithine, lysine, arginine and/or histidine.

Preferred are the potassium salts of the phosphoric acid monoesters mentioned.

Dipotassium monocetyl phosphate is particularly preferred.

Other $C_{12-24}$ alkyl phosphoric esters or salts of $C_{12-24}$ alkyl phosphoric esters preferred as contemplated herein are selected from the diesters of phosphoric acid with lauryl alcohol, tridecyl alcohol, isotridecyl alcohol, myristyl alcohol, pentadecyl alcohol, cetyl alcohol, palmityl alcohol, isocetyl alcohol, isostearyl alcohol, stearyl alcohol, oleyl alcohol, elaidyl alcohol, linoleyl alcohol, linolenyl alcohol, nonadecyl alcohol, arachyl alcohol, gadoleyl alcohol or arachidone alcohol, which are classified as alkali metal alcohol, alkaline earth alcohol, ammonium alcohol, ammonium hydroxide or ammonium hydroxide, alkaline earth, ammonium, alkylammonium, alkanolamine or glucammonium salt, preferably the corresponding sodium, potassium, alkanolamine, trialkylammonium, triethanolamine, 2-amino-1-butanol, 2-amino-2-methyl-1-propanol, 2-amino-2-methyl-1,3-propanediol, 2-amino-2-ethyl-1,3- propanediol or tris-(hydroxymethyl)aminomethane salt and as a salt of the basic amino acids ornithine, lysine, arginine and/or histidine.

Preferred are the potassium salts of said phosphoric diesters.

Potassium dicetyl phosphate is particularly preferred.

In the context of a further very particularly preferred embodiment, an agent as contemplated herein comprises
- (a3) at least one phosphorus-comprising surfactant selected from the group of monoesters of phosphoric acid with a $C_{12}$-$C_{24}$-fatty acid, diesters of phosphoric acid with two $C_{12}$-$C_{24}$-fatty acids, ethoxylated monoesters of phosphoric acid with a $C_{12}$-$C_{24}$-fatty acid, ethoxylated diesters of phosphoric acid with two $C_{12}$-$C_{24}$-fatty acids and salts thereof.

In the context of a further explicitly quite particularly preferred embodiment, an agent as contemplated herein comprises
- (a3) at least one phosphorus-comprising surfactant selected from the group of monoesters of phosphoric acid with a $C_{12}$-$C_{24}$-fatty acid, diesters of phosphoric acid with two $C_{12}$-$C_{24}$-fatty acids, ethoxylated monoesters of phosphoric acid with a $C_{12}$-$C_{24}$-fatty acid, ethoxylated diesters of phosphoric acid with two $C_{12}$-$C_{24}$-fatty acids, potassium salts and sodium salts thereof.

Furthermore, mixtures of mono-$C_{12-20}$ alkyl phosphates and di-$C_{12-20}$ alkyl phosphates can also be used in the agent as contemplated herein.

Furthermore, mixtures of dipotassium monocetyl phosphate and potassium dicetyl phosphate are particularly preferred.

The phosphorus-comprising surfactant(s) or emulsifier(s) (a3) are preferably present in the agent as contemplated herein in certain ranges of amounts. It has proved particularly advantageous regarding solving the problem of the present disclosure if the agent comprises—based on its total weight—one or more phosphorus-comprising surfactants in a total amount of from 0.1 to 20.0 wt. %, preferably from 0.5 to 15.0 wt. 00 more preferably from 1.0 to 10.0 wt. % and very particularly preferably from 1.5 to 8.0 wt. %.

In the context of a further very particularly preferred embodiment, an agent as contemplated herein—based on the total weight of the agent—comprises
- (a3) comprises one or more phosphorus-comprising surfactants in a total amount of from 0.1 to 20.0 wt. %, preferably from 0.5 to 15.0 wt. %, more preferably from 1.0 to 10.0 wt. % and most preferably from 1.5 to 8.0 wt. %.

Particularly preferred agents as contemplated herein contain at least one salt of cetyl phosphate and/or a mixture of dipotassium monocetyl phosphate and potassium dicetyl phosphate in a total amount of from 0.5 to 15.0 wt. %, further preferably from 1.0 to 10.0 wt. % and very particularly preferably from 1.5 to 8.0 wt. %, in each case based on the total weight of the agents.

Corresponding phosphorus-comprising surfactants or emulsifiers comprising mixtures of dipotassium monocetyl phosphate and potassium dicetyl phosphate are commercially available, for example under the name Emulsiphos® 677660 (INCI designation: Potassium Cetyl Phosphate) from the Symrise company.

Furthermore, it has also proved preferable if the agents as contemplated herein contain at least one phosphorus-comprising surfactant (a3) of the formula (I) in which the radical R4 is a saturated or unsaturated, branched or unbranched $C_{12-22}$ alkyl radical, an unsaturated alkyl radical, very preferably an oleyl radical.

In the context of this embodiment, m preferably represents an integer from 0 to 10, an integer from 1 to 5. n preferably represents an integer from 0 to 10, an integer from 0 to 5.

Particularly suitable alkyl phosphoric acid esters (a3) are, for example, the diester of phosphoric acid and ethoxylated lauryl alcohol (INCI designation: Dilaureth-4 phosphates), which is marketed under the trade name Hostaphat® KO 200 and the mixture of mono- and diesters of phosphoric acid and oleyl alcohol (INCI designation: Oleyl Phosphate).

The triester of phosphoric acid and ethoxylated cetearyl alcohol (INCI designation: Triceteareth-4 Phosphate), the triester of phosphoric acid and ethoxylated oleyl alcohol (INCI-designation: Trioleth-8 phosphates) and the triester of phosphoric acid and oleyl alcohol (INCI designation: Trioleyl phosphates).

In the course of the work underlying the present disclosure, it has also been found advantageous if the agent as contemplated herein comprises at least two different optionally alkoxylated alkyl phosphoric acid esters (a3).

Agents comprising at least one dialkyl phosphoric ester and/or at least one ethoxylated monoalkyl phosphoric ester are also preferred as contemplated herein.

Where the agents as contemplated herein contain two different alkyl phosphoric esters (a3), a ratio of ethoxylated monoalkyl phosphoric ester to dialkyl phosphoric ester of 1:5 to 5:1, 1:1 to 2:1, has proved particularly suitable.

A particularly preferred alkyl phosphoric ester combination as contemplated herein is a combination of oleth-5 phosphate with dioleyl phosphate, such as that marketed by Croda under the trade name Crodafos® HCE.

Fat Components in Agent

As a further optional ingredient, the agent as contemplated herein may also additionally comprise at least one fat ingredient.

It has been found that the use of at least one fatty ingredient results in the agent being in the form of an emulsion, which has the optimum viscosity and has also been found to be beneficial in terms of improving hair feel.

The fatty components are hydrophobic substances that can form emulsions in the presence of water, forming micelle systems.

For the purposes of the present disclosure, "fatty components" means organic compounds with a solubility in water at room temperature (22° C.) and atmospheric pressure (760 mmHg) of less than 1 wt. %, preferably less than 0.1 wt. %. The definition of fat constituents explicitly covers only uncharged (i.e., non-ionic) compounds. Fat components have at least one saturated or unsaturated alkyl group with at least 12 C atoms. The molecular weight of the fat constituents is a maximum of 5000 g/mol, preferably a maximum of 2500 g/mol and particularly preferably a maximum of 1000 g/mol. The fat components are neither ethoxylated, nor polyoxyalkylated, nor polyglycerylated compounds.

Very preferably, the fat constituents (a4) included in the agent are selected from the group of $C_{12}$-$C_{24}$ fatty acid triglycerides, $C_{12}$-$C_{24}$ fatty acid monoglycerides, $C_{12}$-$C_{24}$ fatty acid diglycerides, $C_{12}$-$C_{24}$ fatty alcohols and/or hydrocarbons.

In the context of a further very particularly preferred embodiment, an agent as contemplated herein comprises
- (a4) at least one fatty constituent from the group comprising $C_{12}$-$C_{24}$-fatty acid triglycerides, $C_{12}$-$C_{24}$-fatty acid monoglycerides, $C_{12}$-$C_{24}$-fatty acid diglycerides, $C_{12}$-$C_{24}$-fatty alcohols and/or hydrocarbons, particularly preferably $C_{12}$-$C_{24}$-fatty acid triglycerides.

Further, as a suitable fat ingredient, the agent may also contain at least one $C_{12}$-$C_{24}$ fatty acid triglyceride that is $C_{12}$-$C_{24}$ fatty acid monoglyceride and/or $C_{12}$-$C_{24}$ fatty acid diglyceride. For the purposes of the present disclosure, a $C_{12}$-$C_{24}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{24}$ carboxylic acids. Unsaturated fatty acids can be mono- or polyunsaturated. For an unsaturated fatty acid, its C—C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{24}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{24}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{24}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when the agent included at least one $C_{12}$-$C_{24}$-fatty acid monoglyceride selected from the monoesters of glycerol with one equivalent of fatty acid from the group comprising dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselic acid [(Z)-6-octadecenoic acid], Palmitoleic acid [(9Z)-Hexadec-9-enoic acid], Oleic acid [(9Z)—Octadec-9-enoic acid], Elaidic acid [(9E)-Octadec-9-enoic acid], Erucic acid [(13Z)-Docos-13-enoic acid], Linoleic acid [(9Z, 12Z)—Octadeca-9, 12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In the context of a further embodiment, an agent as contemplated herein comprises at least one $C_{12}$-$C_{24}$ fatty acid monoglyceride selected from the monoesters of glycerol with one equivalent of fatty acid from the group comprising dodecanoic acid, tetradecanoic acid, hexadecanoic acid, tetracosanoic acid, octadecanoic acid, eicosanoic acid and/or docosanoic acid.

Preferred $C_{12}$-$C_{24}$ fatty acid monoglycerides and $C_{12}$-$C_{24}$ fatty acid diglycerides as contemplated herein are selected from monomyristoylglyceride, monopalmitoylglyceride, monostearoylglyceride, monoarachinoylglyceride, dimyristoylglyceride, dipalmitoylglyceride, distearoylglyceride and diarachinoylglyceride, and mixtures thereof. Other mixtures preferred as contemplated herein are glycerides of hydrogenated, i.e., hydrogenated, preferably completely hydrogenated, fatty acids of natural oils. Particularly preferred as contemplated herein are hardened (hydrolyzed) palm oil glycerides.

It has been found preferable to use one or more $C_{12}$-$C_{24}$ fatty acid mono-, $C_{12}$-$C_{24}$ fatty acid di- and/or $C_{12}$-$C_{24}$ fatty acid triglycerides in specific ranges of amounts in the agent.

With regard to the solution of the task as contemplated herein, it has proved advantageous if the agent—based on the total weight of the agent—included one or more $C_{12}$-$C_{24}$ fatty acid mono-, $C_{12}$-$C_{24}$ fatty acid di- and/or $C_{12}$-$C_{24}$ fatty acid triglycerides in a total amount of 0.1 to 20.0 wt. %, preferably from 0.3 to 15.0 wt. %, more preferably from 0.5 to 10.0 wt. %, and most preferably from 0.8 to 5.0 wt. %.

Furthermore, in this context, very particularly preferred fat constituents are understood to be constituents from the group of $C_{12}$-$C_{24}$ fatty alcohols, $C_{12}$-$C_{24}$ fatty acid triglycerides, $C_{12}$-$C_{24}$ fatty acid monoglycerides, $C_{12}$-$C_{24}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{24}$ fatty alcohols can be saturated, mono- or polyunsaturated, linear or branched fatty alcohols with 12 to 24 C atoms.

Examples of preferred linear, saturated $C_{12}$-$C_{24}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In another preferred embodiment, an agent as contemplated herein comprises one or more $C_{12}$-$C_{24}$ fatty alcohols selected from the group of. Dodecan-1-ol (dodecyl alcohol, lauryl alcohol), Tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), Behenyl alcohol (docosan-1-ol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), Gadoleyl alcohol ((9Z)-Eicos-9-en-1-ol), Arachidone alcohol ((5Z,8Z,11Z,14Z)-Eicosa-5,8,11,14-tetraen-1-ol), Erucyl alcohol ((13Z)-Docos-13-en-1-ol), Brassidyl alcohol ((13E)-docosen-1-ol) 2-octyl-dodecanol, 2-hexyl-dodecanol and/or 2-butyl-dodecanol. 2-Butyl-dodecanol comprises.

It has been found to be quite preferable to use one or more $C_{12}$-$C_{24}$ fatty alcohols in quite specific ranges of amounts.

It is particularly preferred if the agent comprises one or more $C_{12}$-$C_{24}$ fatty alcohols in a total amount—based on the total weight of the agent—of from 2.0 to 50.0 wt. %, preferably from 3.0 to 30.0 wt. %, more preferably from 4.0 to 20.0 wt. %, still more preferably from 5.0 to 15.0 wt. %, and most preferably from 5.0 to 10.0 wt. %.

Furthermore, as a very particularly preferred fat constituent, the agents may also contain at least one hydrocarbon.

Hydrocarbons are compounds comprising exclusively of the atoms carbon and hydrogen with 8 to 80 C atoms. In this context, aliphatic hydrocarbons such as mineral oils, liquid paraffin oils (e.g., Paraffinum Liquidum or Paraffinum Perliquidum), isoparaffin oils, semi-solid paraffin oils, paraffin waxes, hard paraffin (Paraffinum Solidum), Vaseline and polydecenes are particularly preferred.

Liquid paraffin oils (Paraffinum Liquidum and Paraffinum Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, comprising hydrocarbon chains with a C-chain distribution of 25 to 35 C-atoms.

Particularly satisfactory results were obtained when the agent included at least one hydrocarbon selected from the group of mineral oils, liquid kerosene oils, isoparaffin oils, semisolid kerosene oils, kerosene waxes, hard kerosene (Paraffinum solidum), petrolatum and polydecenes.

In a very particularly preferred embodiment, an agent as contemplated herein comprises—based on the total weight of the agent—one or more hydrocarbons in a total amount of in a total amount of from 0.5 to 20.0 wt. %, preferably from 0.7 to 10.0 wt. %, more preferably from 0.9 to 5.0 wt. % and very particularly preferably from 1.0 to 4.0 wt. %.

The fat constituent(s) described above may be added as separate ingredients to the agents of the present disclosure. Furthermore, however, it has also proved to be particularly advantageous if the phosphorus-comprising surfactant(s) (a3) is/are purchased commercially in the form of a commercial product which is a blend with at least one fatty constituent.

Thus, in addition to the mixture of dipotassium monocetyl phosphate and potassium dicetyl phosphate, the very particularly preferred commercially available raw material Emulsiphos® 677660 further comprises Hydrogenated palm oil glycerides (INCI designation: Potassium Cetyl Phosphate, Hydrogenated Palm Glycerides), i.e., a mixture of $C_{12}$-$C_{24}$ fatty acid glycerides. Emulsiphos® 677660 from Symrise is commercially available.

Water Content in Agent

The agent described above is a ready-to-use agent that can be applied to the keratinous material. This ready-to-use agent preferably has a high water content. It has been found that particularly suitable agents are those comprising—based on the total weight of the agent—50.0 to 98.0 wt. %, preferably 60.0 to 90.0 wt. %, more preferably 70.0 to 90.0 wt. % and most preferably 75.0 to 90.0 wt. % of water.

In a further explicitly quite particularly preferred embodiment, an agent as contemplated herein comprises—based on the total weight of the agent—50.0 to 98.0 wt. %, preferably 60.0 to 90.0 wt. %, further preferably 70.0 to 90.0 wt. % and very particularly preferably 75.0 to 90.0 wt. % of water.

Other Optional Ingredients in the Agent

In addition to the ingredients (a1) to (a3) essential to the present disclosure already described, the agent may also contain further optional ingredients.

For example, the agent may contain a film-forming polymer. The film-forming polymer may be selected, for example, from the group comprising polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further suitable film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of olefins, such as cycloolefins, butadiene, isoprene or styrene, vinyl ethers, vinyl amides, the esters or amides of (meth)acrylic acid having at least one $C_1$-$C_{20}$ alkyl group, an aryl group or a $C_2$-$C_{10}$ hydroxyalkyl group.

Other film-forming polymers may be selected from the homo- or copolymers of isooctyl (meth)acrylate; isononyl (meth)acrylate; 2-ethylhexyl (meth)acrylate; lauryl (meth)acrylate); isopentyl (meth)acrylate; n-butyl (meth)acrylate); isobutyl (meth)acrylate; ethyl (meth)acrylate; methyl (meth)acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth)acrylamides, in those with C2-C18 alkyl groups, such as N-ethyl-acrylamide, N-tert-butyl-acrylamide, le N-octyl-acrylamide; N-di(C1-C4)alkyl-(meth)acrylamide.

Other suitable anionic copolymers include copolymers of acrylic acid, methacrylic acid or their $C_1$-$C_6$ alkyl esters, as sold under the INCI declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Polymers on the market include Aculyn® 22 (Acrylate/Steareth-20 Methacrylate Copolymer), Aculyn® 28 (Acrylate/Beheneth-25 Methacrylate Copolymer), Structure 2001® (Acrylates/Steareth-20 Itaconate Copolymer), Structure 3001@(Acrylate/Ceteth-20 Itaconate Copolymer), Structure Plus® (acrylate/aminoacrylate $C_{10\text{-}30}$ alkyl PEG-20 itaconate copolymer), Carbopol® 1342, 1382, Ultrez 20, Ultrez 21 (acrylate/$C_{10\text{-}30}$ alkyl acrylate crosspolymer), Synthalen W 2000® (acrylate/palmeth-25 acrylate copolymer) or Soltex OPT (acrylate/$C_{12\text{-}22}$ alkyl methacrylate copolymer) distributed by Rohme und Haas.

The homo- and copolymers of N-vinylpyrrolidone, vinylcaprolactam, vinyl-($C_1$-$C_6$)alkyl-pyrrole, vinyl-oxazole, vinyl-thiazole, vinylpyrimidine, vinylimidazole can be named as suitable polymers based on vinyl monomers.

Also suitable are the copolymers octylacrylamide/acrylates/butylaminoethyl methacrylate copolymer, such as those sold commercially under the trade names AMPHOMER® or LOVOCRYL® 47 from NATIONAL STARCH, or the copolymers of acrylates/octylacrylamides sold under the trade names DERMACRYL® LT and DERMACRYL® 79 from NATIONAL STARCH.

Suitable olefin-based polymers include homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

If, in principle, both anionic and cationic and/or non-ionic polymers can be used in the agent as contemplated herein, it has proved particularly preferable not to use further ionic compounds or to use them only in lesser amounts. In other words, a particularly strong improvement in color intensity could be achieved when the agent was a non-ionic base and therefore included cationic and anionic polymers either not at all or only in lesser amounts. For this reason, it has been found to be particularly preferable if the total content of all anionic polymers included in the agent is below 0.1 wt. %. Furthermore, it has been found to be particularly preferred if the total content of all cationic polymers included in the agent is below 0.1 wt. %. The amount of catalytic or anionic polymer is related to the total weight of the agent.

In another very particularly preferred embodiment, an agent as contemplated herein comprises—in relation to the total weight of the agents
the total content of all anionic polymers included in the agent is below 0.1 wt. %, and
the total content of all cationic polymers included in the agent is below 0.1 wt. %.

Zwitterionic surfactants are those surface-active compounds which carry at least one quaternary ammonium group and at least one —COO$^{(-)}$— or —SO$_3^{(-)}$ group in the molecule. Particularly suitable zwitterionic surfactants are the so-called betaines such as the N-alkyl-N,N-dimethylammoniumglycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —SO$_3$H group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Examples of ampholytic surfactants are N-cocosalkylaminopropionate, cocosacylaminoethylaminopropionate and $C_{12}$-$C_{18}$-acyl sarcosine.

In addition, the agents may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually comprising a hydrocarbon backbone (e.g., comprising one or two linear or branched alkyl chains) and the positive charge(s) being in the hydrophilic head group. Examples of cationic surfactants are
quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %-based on the total weight of the respective agent.

Furthermore, the agent as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

If, in principle, both anionic and cationic and/or non-ionic surfactants can be used in the agent as contemplated herein, it has proved particularly preferable not to use further ionic compounds or to use them only in small quantities. In other words, a particularly strong improvement in color intensity could be achieved when the agent was a non-ionic base and therefore included cationic and anionic surfactants either not at all or only in lesser amounts. For this reason, it has been found to be particularly preferable if the total content of all anionic surfactants included in the agent is below 0.1 wt. %. Furthermore, it has been found to be particularly preferable if the total content of all cationic surfactants included in the agent is below 0.1 wt. %. The amount of catalytic or anionic surfactant is related to the total weight of the product.

In another very particularly preferred embodiment, an agent as contemplated herein comprises—in relation to the total weight of the agents the total content of all anionic surfactants included in the agent is below 0.1 wt. %, and the total content of all cationic surfactants included in the agent is below 0.1 wt. %.

The agents may also contain other active ingredients, auxiliaries and additives, such as solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosene; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

Agent pH Value

The pH of the agent as contemplated herein can be adjusted to a slightly acidic to alkaline pH. Most preferably, the agent has a pH in the range of 5.0 to 10.0, preferably 6.0 to 9.5, more preferably 6.0 to 8.7, and most preferably 6.0 to 7.5.

Within the scope of a further preferred embodiment, an agent as contemplated herein further comprises water and has a pH of from 5.0 to 10.0, preferably from 6.0 to 9.5, more preferably from 6.0 to 8.7, and most preferably from 6.0 to 7.5.

Alkalizing agents and acidifying agents known to the skilled person can be used to adjust the desired pH value. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment of the agent as contemplated herein comprises an alkanolamine selected from 2-aminoethan-1-ol and/or 2-amino-2-methylpropan-1-ol as alkalizing agent.

For the purposes of the present disclosure, an amino acid is an organic compound comprising at least one protonatable amino group and at least one —COOH or —$SO_3H$ group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein comprises the alkalizing agent that is a basic amino acid chosen from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Also, as contemplated herein, the desired pH value can be adjusted by employing a buffer system. A buffer or buffer system is usually understood to be a mixture of a weak or medium-strength acid (e.g., acetic acid) with a completely dissociated neutral salt of the same acid (e.g., sodium acetate). If some base or acid is added, the pH value hardly changes (buffering). The effect of the buffer substances included in a buffer solution is based on the scavenging reaction of hydrogen or hydroxide ions with the formation of weak acids or bases due to their dissociation equilibrium.

A buffer system can be formed from a mixture of an inorganic or organic acid and a corresponding salt of that acid.

Acids can be buffered by all salts of weak acids and strong bases, bases by salts of strong acids and weak bases. The strong hydrochloric acid (completely dissociated into ions) can be buffered, for example, by adding sodium acetate. According to the balance

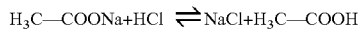

hydrochloric acid is converted by sodium acetate to the weak acetic acid with the formation of sodium chloride, which dissociates only to a small extent in the presence of an excess of sodium acetate. Buffers that are effective against both acids and bases are mixtures of weak acids and their salts.

Examples of buffer systems known from the literature are acetic acid/sodium acetate, boric acid/sodium borate, phosphoric acid/sodium phosphate and hydrogen carbonate/soda.

The pH of the agent as contemplated herein can be adjusted, for example, by adding an inorganic or organic buffer system. For the purposes of the present disclosure, an inorganic buffer system is understood to be a mixture of an inorganic acid and its conjugate corresponding inorganic base.

For the purposes of the present disclosure, an organic buffer system is understood to be a mixture of an organic acid and its conjugate corresponding base. Due to the organic acid radical, the conjugate corresponding base of the organic acid is also organic. Here, the cation presents to neutralize the charge of the acid anion can be inorganic or organic.

Examples of inorganic acids are sulfuric acid, hydrochloric acid and phosphoric acid ($H_3PO_4$). Phosphoric acid is a medium-strength acid that is particularly preferred.

A particularly well-suited inorganic acid is potassium dihydrogen phosphate
Potassium dihydrogen phosphate has the molecular formula $KH_2PO_4$ and carries the CAS number 7778-77-0. Potassium dihydrogen phosphate has a molar mass of 136.09 g/mol. It is highly soluble in water (222 g/l at 20° C.) and reacts acidically in water. A 5% solution of potassium dihydrogen phosphate in water has a pH value of 4.4.

Another particularly suitable inorganic acid is sodium dihydrogen phosphate. Sodium dihydrogen phosphate has the molecular formula $NaH_2PO_4$ and carries the CAS numbers 7558-80-7 (anhydrate), 10049-21-5 (monohydrate) and 13472-35-0 (dihydrate). The anhydrous sodium dihydrogen phosphate has a molar mass of 119.98 g/mol. Sodium dihydrogen phosphate reacts acidically in aqueous solution.

Particularly preferred as a corresponding salt of the above two acids are dipotassium hydrogen phosphate. Dipotassium hydrogen phosphate has the molecular formula $K_2HPO_4$ and carries the CAS numbers 7758-11-4 (anhydrous) and 16788-57-1 (trihydrate). The anhydrous dipotassium hydrogen phosphate has a molar mass of 174.18 g/mol. Dipotassium hydrogen phosphate reacts alkaline in aqueous solution.

Also particularly preferred as a corresponding salt of the above two acids are disodium hydrogen phosphate. Disodium hydrogen phosphate has the molecular formula $Na_2HPO_4$ and carries the CAS numbers 7558-79-4 (anhydrous), 10028-24-7 (dihydrate), 7782-85-6 (heptahydrate) and 10039-32-4 (dodecahydrate). Anhydrous disodium hydrogen phosphate has a molar mass of 141.96 g/mol. Disodium hydrogen phosphate reacts alkaline in aqueous solution.

Examples of organic acids are citric acid, succinic acid, tartaric acid, lactic acid, acetic acid, malic acid, malonic acid and maleic acid.

Examples of the corresponding salts of these organic acids are the sodium and potassium salts of citric acid, the sodium and potassium salts of succinic acid, the sodium and potassium salts of tartaric acid, sodium and potassium salts of lactic acid, sodium and potassium salts of acetic acid, sodium and potassium salts of malic acid, sodium and potassium salts of malonic acid and sodium and potassium salts of maleic acid.

Process for Dyeing Keratin Material

The agents described above can be excellently used in processes for dyeing keratinous material, especially human hair.

A second object of the present disclosure is therefore a method for coloring keratinous material, in particular human hair, comprising the following steps:

(1) Application of a coloring agent to the keratinous material, wherein the coloring agent is an agent as disclosed in detail in the description of the first subject matter of the present disclosure, (2) Exposure of the colorant to the keratinous material and (3) Rinse out the dye with water.

In step (1) of the process as contemplated herein, the agent of the first present disclosure is applied to the keratinous material, which is most preferably human hair.

In step (2) of the process as contemplated herein, the agent is then allowed to act on the keratinous material after its application. In this context, different exposure times of, for example, 30 seconds to 60 minutes are conceivable.

However, a major advantage of the dyeing system as contemplated herein is that an intensive color result can be achieved even in short periods after short exposure times. For this reason, it is advantageous if the application mixture remains on the keratin material only for comparatively short periods of time after its application, from 30 seconds to 15 minutes, preferably from 30 seconds to 10 minutes, and particularly preferably from 1 to 5 minutes.

In a further preferred embodiment, a method as contemplated herein comprises (2) Exposing the keratinous material to a colorant for a period ranging from 30 seconds to 15 minutes, preferably from 30 seconds to 10 minutes, and most preferably from 1 to 5 minutes.

Finally, following the action of the application mixture on the keratin material, it is rinsed with water in step (3) of the process.

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the convenience of use, it has proved particularly preferable to rinse the agent in step (3) exclusively with water without the aid of a further after-treatment agent, shampoo or conditioner.

In a further preferred embodiment, a method as contemplated herein comprises (3) Rinsing out the colorant from the keratinous material with water only.

Concerning the further preferred embodiments of the method as contemplated herein, mutatis mutandis what has been said about the agents as contemplated herein applies.

EXAMPLES

1. Formulations

The following formulations were prepared (all data in wt. % unless otherwise stated):

| Colorants | (V1) | (E1) | (E2) |
|---|---|---|---|
| Cetyl alcohol | 3.0 | 3.0 | 3.0 |
| $C_{12}$-$C_{18}$-fatty alcohols (Lorol techn.) | 3.0 | 3.0 | 3.0 |
| Phenoxyethanol | 0.8 | 0.8 | 0.8 |
| Sodium salicylate | 0.4 | 0.4 | 0.4 |
| Unipure Red LC 3071 (CI 15850) | 1.0 | 1.0 | 1.0 |
| Dow Corning 2-8566 (Siloxanes and Silicones, 3-[(2-Aminoethyl)amino]-2-methylpropyl Me, Di-Me-Siloxane" | 1.0 | 1.0 | 1.0 |
| 1.2-propanediol | 10.0 | 10.0 | 10.0 |
| Potassium dihydrogen phosphate | 0.35 | 0.35 | 0.35 |
| Disodium hydrogen phosphate | 0.72 | 0.72 | 0.72 |
| Ceteareth-30 (Cetearyl alcohol, ethoxylated 30 EO) | 3.0 | — | — |
| Emulsiphos 677660 (INCI designation: Potassium Cetyl Phosphate, Hydrogenated Palm Glycerides), Symrise | — | 3.0 | — |
| Crodafos ® HCE (INCI designation: Oleth-5 phosphate with dioleyl phosphate), Croda | — | — | 3.0 |
| Water | ad 100 | ad 100 | ad 100 |

2. Application

After preparation, the respective agent (V1, E1 and E2) was applied to hair strands (Kerling, Euronatural hair white, liquor ratio: 1 g agent per g hair strand) applied. The agent was left to act for three minutes. Subsequently, the hair strands were thoroughly washed (1 minute) with water, dried, and then evaluated by trained individuals in terms of hair feel.

| Colorants | (V1) | (E1) | (E2) |
|---|---|---|---|
| Hair feeling | occupied, heavy, unnatural, straw, | soft, smooth, natural | soft, smooth, natural |
| Coloring | red +++ | red +++ | red +++ |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Agent for dyeing keratinous material, comprising:
   (a1) at least one amino-functionalized silicone polymer,
   (a2) at least one pigment,
   (a3) at least one phosphorus-containing surfactant selected from the group of monoesters of phosphoric acid with a $C_{12}$-$C_{24}$-fatty acid, diesters of phosphoric acid with two $C_{12}$-$C_{24}$-fatty acids, ethoxylated monoesters of phosphoric acid with a $C_{12}$-$C_{24}$-fatty acid, ethoxylated diesters of phosphoric acid with two $C_{12}$-$C_{24}$-fatty acids and salts thereof; and
   (a4) at least one fatty constituent from the group of $C_{12}$-$C_{24}$-fatty acid triglycerides, $C_{12}$-$C_{24}$-fatty acid monoglycerides, $C_{12}$-$C_{24}$-fatty acid diglycerides, $C_{12}$-$C_{24}$-fatty alcohols and/or hydrocarbons.

2. The agent according to claim 1, wherein the at least one amino-functionalized silicone polymer (a1) comprises at least one secondary amino group.

3. The agent according to claim 1, wherein the at least one amino-functionalized silicone polymer (a1) comprises at least one structural unit of the formula (Si amino),

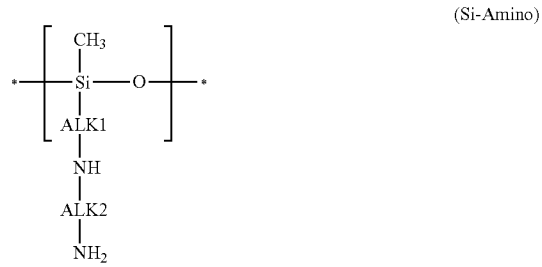

where
ALK1 and ALK2 independently represent a linear or branched $C_1$-$C_{20}$ divalent alkylene group.

4. The agent according to claim 1, wherein the at least one amino-functionalized silicone polymer (a1) comprises structural units of the formula (Si-I) and of the formula (Si-II)

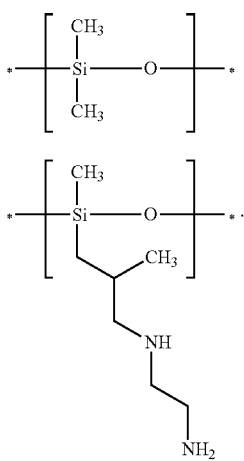

5. The agent according to claim 1, comprising—based on the total weight of the agent—the at least one amino-functionalized silicone polymer(s) (a1) in a total amount of from 0.1 to 8.0 wt. %.

6. The agent according to claim 1, wherein the at least one pigment (a2) is chosen from the group of colored metal oxides, metal hydroxides, metal oxide hydrates, silicates, metal sulfides, complex metal cyanides, metal sulfates, bronze pigments, and/or mica- or mica-based colored pigments coated with: at least one metal oxide and/or a metal oxychloride.

7. The agent according to claim 1, wherein the at least one pigment (a2) is chosen from the group of carmine, quinacridone, phthalocyanine, Sorgho, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

8. The agent according to claim 1, comprising—based on the total weight of the agent (a)—the at least one pigment(s) (a2) in a total amount of from 0.01 to 10.0 wt. %.

9. The agent according to claim 1, wherein the at least one phosphorus-containing organic compound (a3) comprises at least one phosphorus-containing surfactant.

10. The agent according to claim 1, wherein the at least one phosphorus-containing organic compound (a3) comprises at least one alkyl phosphoric ester of the formula (I)

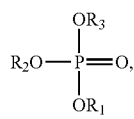

where
$R_1$, $R_2$ and $R_3$ are independently hydrogen, an alkali metal cation, an ammonium ion or a radical of formula (II)

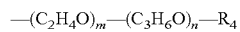

m and n independently of each other stand for an integer from 0 to 20, and
$R_4$ is a saturated or unsaturated, branched or unbranched $C_{12-24}$ alkyl radical,
with the proviso that at least one of the radicals $R_1$, $R_2$ or $R_3$ is a radical of the formula (II).

11. The agent according to claim 1, wherein the at least one phosphorus-containing organic compound (a3) comprises
(a3) at least one phosphorus-containing surfactant selected from the group of monoesters of phosphoric acid with a $C_{12}$-$C_{24}$-fatty acid, diesters of phosphoric acid with two $C_{12}$-$C_{24}$-fatty acids, ethoxylated monoesters of phosphoric acid with a $C_{12}$-$C_{24}$-fatty acid, ethoxylated diesters of phosphoric acid with two $C_{12}$-$C_{24}$-fatty acids and salts thereof.

12. The agent according to claim 1, comprising—based on the total weight of the agent
(a3) one or more phosphorus-containing surfactants in a total amount of from 0.1 to 20.0% by weight.

13. The agent according to claim 1, further comprising water, wherein the agent has a pH of from 5.0 to 10.0.

14. A process for dyeing keratinous material comprising the following steps:
(1) Applying a colorant according to claim 1 to the keratinous material,
(2) Exposing the keratinous material to a colorant and
(3) Rinsing the colorant from the keratinous material with water.

15. The method according to claim 14, wherein (2) Exposing the keratinous material to the colorant comprises
(2) Exposing the keratinous material to the colorant for a period ranging from 30 seconds to 15 minutes.

16. The agent according to claim 5, wherein
the at least one amino-functionalized silicone polymer (a1) comprises structural units of the formula (Si-I) and of the formula (Si-II)

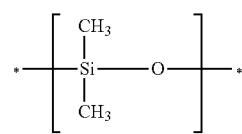

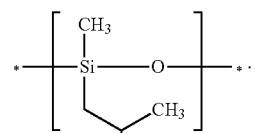

17. The agent according to claim 16, comprising—based on the total weight of the agent:
   the at least one amino-functionalized silicone polymer(s) (a1) in a total amount of from 0.4 to 2.5 wt. %;
   the at least one pigment(s) (a2) in a total amount of from 0.25 to 1.5 wt. %; and
   the one or more phosphorus-containing organic compound(s) in a total amount of from 1.5 to 8.0 wt. %.

18. The agent according to claim 17, wherein the at least one phosphorus-containing organic compound (a3) comprises at least one alkyl phosphoric ester of the formula (I)

(I)

where
$R_1$, $R_2$ and $R_3$ are independently hydrogen, an alkali metal cation, an ammonium ion or a radical of formula (II)

—$(C_2H_4O)_m$—$(C_3H_6O)_n$—$R_4$  (II), m and n independently of each other stand for an integer from 0 to 20, and
$R_4$ is a saturated or unsaturated, branched or unbranched $C_{12-24}$ alkyl radical,
with the proviso that at least one of the radicals $R_1$, $R_2$ or $R_3$ is a radical of the formula (II).

* * * * *